United States Patent [19]

Torii et al.

[11] Patent Number: 4,588,835

[45] Date of Patent: May 13, 1986

[54] PROCESS FOR PREPARING ALKOXYPHENOLS

[75] Inventors: Sigeru Torii; Hideo Tanaka, both of Okayama; Mitsuo Akada, Naruto, all of Japan

[73] Assignee: Otsuka Kagaku Yakuhin Kabushiki Kaisha, Osaka, Japan

[21] Appl. No.: 662,542

[22] Filed: Oct. 19, 1984

Related U.S. Application Data

[63] Continuation of Ser. No. 362,890, Mar. 29, 1982, abandoned, which is a continuation-in-part of Ser. No. 132,991, Mar. 24, 1980, abandoned.

[51] Int. Cl.⁴ .................... C07C 41/16; C07C 45/64; C07C 67/28
[52] U.S. Cl. .................... 560/254; 568/433; 568/592; 568/650; 568/651; 568/652
[58] Field of Search ............ 568/650, 651, 652, 433, 568/592; 560/254

[56] References Cited

U.S. PATENT DOCUMENTS 3,479,381 11/1969 Mitchell .............................. 568/851
4,172,960 10/1979 Baldwin et al. ..................... 568/772

OTHER PUBLICATIONS

Morton, Laboratory Technique in Organic Chemistry (1938), 2-7.
Bulgach et al., Chem. Abs., vol. 30 (1936), 3836 (2).

*Primary Examiner*—Bernard Helfin
*Attorney, Agent, or Firm*—Armstrong, Nikaido, Marmelstein & Kubovcik

[57] ABSTRACT

A process for preparing an alkoxyphenol represented by the formula:

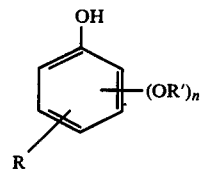

wherein R is hydrogen, alkyl having 1 to 4 carbon atoms, formyl, hydroxymethyl, alkoxymethyl, dialkoxymethyl, acetoxymethyl or diacetoxymethyl, R' is alkyl having 1 to 4 carbon atoms, and n is an integer of 1 to 5, characterized in that a phenol halide represented by the formula:

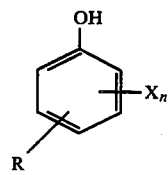

wherein R and n are as defined above, and X is chlorine or bromine is reacted, in the presence of a copper salt serving as a catalyst and of a solvent, with a product prepared by heating, in the presence of a dehydrating agent, an alkali metal hydroxide and a compound of the formula R'OH wherein R' is as defined above.

5 Claims, No Drawings

PROCESS FOR PREPARING ALKOXYPHENOLS

This application is a continuation of application Ser. No. 362,890, filed Mar. 29, 1982, which is a continuation-in-part application of Ser. No. 132,991 filed Mar. 24, 1980, both of which are now abandoned.

This invention relates to a process for preparing alkoxyphenols, and more particularly to a process for preparing alkoxyphenols from phenol halides.

Processes are well known for preparing alkoxyphenols from phenol halides, in other words, for substituting alkoxyl groups for the halogen substituents in phenols. Usually alkoxyphenols are produced by reacting with heating a phenol halide with an alcoholate prepared by dissolving metallic sodium in an alcohol, in a suitable solvent, such as dimethylformamide or an amine, in the presence of a copper halide serving as a catalyst. Laid-Open West German Patent Application No. 2627874 and Chemical Abstract 86, 171074 (1974), for example, disclose a process for synthesizing pyrogallol in which 2,6-dibromo-4-tert-butylphenol is reacted with sodium methoxide with use of copper iodide as a catalyst and dimethylformamide as a solvent to afford 2,6-dimethoxy-4-tert-butylphenol in a yield of 89%. Journal of Chemical Society (C), 312 (1969) further discloses that several kinds of aromatic halides, including phenol bromide, are reacted with sodium methoxide in a mixture of methanol and collidine with use of copper iodide as a catlyst to give the corresponding methoxidated aromatic compounds in yields of 37 to 99%.

With the conventional processes, the alcoholates used are all those prepared by dissolving metallic sodium in alcohols. The preparation of alcoholates nevertheless requires the use of expensive alkali metals, needs special care for handling and therefore is not always preferable.

An object of the invention is to provide a process for preparing alkoxyphenols from corresponding phenol halides with use of compounds which are easy to handle.

Another object of the invention is to provide a process for preparing alkoxyphenols from phenol halides with use of compounds which are inexpensive and readily available.

These objects and other features of the invention will become apparent from the following description.

The present invention provides a process for preparing an alkoxyphenol represented by the formula

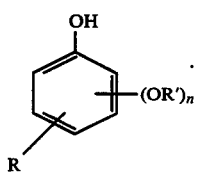

wherein R is hydrogen, alkyl having 1 to 4 carbon atoms, formyl, hydroxymethyl, alkoxymethyl, dialkoxymethyl, acetoxymethyl or diacetoxymethyl, R' is alkyl having 1 to 4 carbon atoms, and n is an integer of 1 to 5, characterized in that a phenol halide represented by the formula

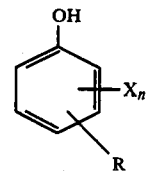

wherein R and n are as defined above, and X is chlorine or bromine is reacted, in the presence of a copper salt serving as a catalyst and of a solvent, with a product prepared by heating, in the presence of a dehydrating agent, an alkali metal hydroxide and a compound of the formula R'OH wherein R' is as defined above.

According to the invention it is critical that a phenol halide of the foregoing formula be reacted with a product obtained by heating an alkali metal hydroxide and a compound of the formula R'OH wherein R' is as defined above, in the presence of a dehydrating agent.

Thus the process of this invention is practiced with use of an alkali metal hydroxide which is extremely inexpensive and easy to handle, in place of alcoholates prepared from an alkali metal and an alcohol and heretofore used. The present process is therefore free of any of the drawbacks attributable to the use of alkali metal. It is also noteworthy that the yield of the desired alkoxyphenol is comparable or even superior to those attained with use of alcoholates of alkali metal.

It is known that an alkali metal hydroxide and an alcohol, when heated, undergo the following equilibrium reaction:

$$MOH + R'OH \rightleftharpoons MOR' + H_2O$$

wherein M is an alkali metal, and R' is as defined above. Since this reaction produces MOR' in a very small amount, it is almost impossible to separate out only MOR' for practical use. Although removal of the resulting water will permit the reaction to proceed toward the right side, the dehydrating agents heretofore known are unable to effect dehydration to such an extent as to render MOR' separable for actual use.

The present invention is based on the novel finding that the product obtained by heating an alkali metal hydroxide and an alcohol of the foregoing formula in the presence of a dehydrating agent, as separated or without being separated from the dehydrating agent, (hereinafter referred to as "first-step reaction product") is effective for preparing alkoxyphenols from phenol halides. In fact, we have found that the first-step reaction product, which is entirely different in composition from the pure alcoholates heretofore used, is effectively usable for the preparation of alkoxyphenols from phenol halides and, still more surprisingly, that the use of the first-step reaction product affords the desired product in as high a yield as is achieved by the use of pure alcoholates.

The first-step reaction product can be prepared by heating 1 to 20 moles, preferably 3 to 10 moles, per mole of the phenol halide of an alkali metal hydroxide and 1 to 50 moles, preferably 5 to 40 moles, per mole of the alkali metal hydroxide of a compound R'OH in the presence of a dehydrating agent at a temperature of 5° to 200° C., preferably at reflux temperature. The dehydrating agent is used in an amount of 0.5 to 50 times, preferably 5 to 30 times, the amount by weight of the phenol halide. The heating time, although dependent on the temperature, is usually 0.5 to 24 hours, preferably 2 to 15 hours. At reflux temperature, it is about 2 to about 15 hours. Since the dehydrating agent used for the first-step reaction produces no adverse effect on the subsequent alkoxylation of the phenol halide, the agent need not be removed from the resulting product, but the agent may be removed. Although the first-step reaction product still remains to be fully clarified with respect to its components or composition, the product presumably is a mixture of alcoholate, alkali metal hydroxide, dehydrating agent, hydroxide of the agent, etc. The product is effectively usable for the present process insofar as it is prepared under the conditions described. Examples of alkali metal hydroxides useful for the preparation of the first-step reaction product are sodium hydroxide, potassium hydroxide, lithium hydroxide, etc. These hydroxides should not be used in the form of an aqueous solution. Examples of useful alcohols represented by R'OH wherein R' is as defined above are methyl alcohol, ethyl alcohol and n-propyl alcohol, and further include isopropyl alcohol and tertiary butyl alcohol. Examples of useful dehydrating agents are oxides of alkaline earth metals, such as calcium oxide and magnesium oxide, anhydrous sulfates of alkali metals or alkaline earth metals, such as anhydrous sodium sulfate and anhydrous magnesium sulfate, silica gel, molecular sieves, active alumina, etc.

With this invention, the first-step reaction product is reacted with a phenol halide to obtain the desired alkoxyphenol. Examples of useful phenol halides of the foregoing formula are 2-chlorophenol, 2-bromophenol, 2,4-dichlorophenol, 2,4-dibromophenol, 2,5-dichlorophenol, 2,5-dibromophenol, 2,4,5-trichlorophenol, 2,4,5-tribromophenol, 2,4,6-trichlorophenol, 2,4,6-tribromophenol, 2-chloro-4-methylphenol, 2-bromo-4-methylphenol, 2,6-dichloro-4-methylphenol, 2,6-dibromo-4-methylphenol, 2-chloro-4-tert-butylphenol, 2-bromo-4-tert-butylphenol, 2,6-dichloro-4-tert-butylphenol, 2,6-dibromo-4-tert-butylphenol, 3-methyl-4-chlorophenol, 3-methyl-4-bromophenol, 3-methyl-4,6-dichlorophenol, 3-methyl-4,6-dibromophenol, 3-tert-butyl-4-chlorophenol, 3-tert-butyl-4-bromophenol, 3-tert-butyl-4,6-dichlorophenol, 3-tert-butyl-4,6-dibromophenol, 3-chloro-4-hydroxybenzaldehyde, 3-bromo-4-hydroxybenzaldehyde, 3-chloro-4-hydroxybenzylalcohol, 2-chloro-4-methoxyphenol, 2-bromo-4-methoxymethylphenol, 2-chloro-4-ethoxymethylphenol, 2-chloro-4-dimethoxymethylphenol, 2-bromo-4-dimethoxymethylphenol, 2-chloro-4-acetoxymethylphenol, 2-bromo-4-acetoxymethylphenol, 2-chloro-4-diacetoxymethylphenol, 2-bromo-4-diacetoxymethylphenol.

For the reaction of the phenol halide and the first-step reaction product according to the invention, 1 to 10 mole, preferably 1 to 5 mole, of the product is admixed with 1 mole of the phenol halide, and the mixture is heated usually at 50° to 150° C., preferably about 100° to 120° C. For this reaction, suitable solvents are usable. Examples of useful solvents are amines, such as pyridine, lutidine, collidine, etc., and amides, such as dimethylformamide, dimethylacetamide, hexamethylsulfonamide, etc., among which amides are preferable to use. Such solvents are used in about 1 to 50 times, preferably about 10 to 30 times, the amount by weight of the phenol halide. Although copper salts need not always be used as catalysts in the present process, copper salts, if used, will result in an increased reaction velocity. While any of the known copper salts is usable, examples of preferable copper salts are mono-or di-valent copper halides, such as copper chloride, copper bromide and copper iodide. These copper salts are used in an amount of 1 to 50% by weight, preferably 20 to 30% by weight, based on the phenol halide.

The process of the invention can be practiced with use of a reactor equipped with a usual reflux condenser, or by heating the bottom of a reactor with the starting mixture placed therein while recovering the solvent on spontaneous evaporation.

Vanillin and other compounds useful as flavors for foods can be produced at a low cost and with ease from the alkoxyphenols prepared by the present process.

The invention will be described in greater detail with reference to the following examples.

EXAMPLE 1

Preparation of 2-methoxy-4-methoxymethylphenol

To 1.16 g (20.7 m mol) of calcined calcium oxide were added 6 ml of dried methanol and 340 mg (8.5 m mol) of sodium hydroxide and then the mixture was refluxed for 12 hours on an oil bath. The mixture was left to stand and 3 ml of the supernatant was taken off from the reflux by a dried injection, and, the supernatant thus withdrawn, after weighing out, was added to 89.0 mg (0.410 m mol) of 2-bromo-4-methoxymethylphenol dried beforehand. To the resulting mixture were added 1.5 ml of dried dimethylformamide and 24 mg of anhydrous cupric chloride and the resulting mixture was placed in an reactor in which the air was exchanged with nitrogen gas. While the bottom part of the reactor was dipped in an oil bath heated at 110° C., the mixture was stirred for 4.5 hours at 110°–118° C. to evaporate the solvent.

The remaining solvent was further distilled off from the reaction mixture thus obtained. Then 5 ml of 5% HCl solution was added to the above product and the resulting mixture was extracted with 30 ml of ether. The extract was washed with saturated sodium chloride solution and dried to produce 99.0 mg of yellowish oily liquid. The liquid was developed with a mixture of hexane-benzene-ethyl acetate (20:1) on a silica gel column to produce 65.9 mg (95.6% in yield) of 2-methoxy4-methoxymethylphenol.

IR (neat): 3740, 2944, 2865, 2834, 1613, 1507, 1466, 1433, 1372, 1277, 1240, 1154, 1086, 1032, 852, 815, 793 cm$^{-1}$.

NMR(CCl$_4$): $\delta$3.27 (S,3H, —C—OCH$_3$), 3.81 (S,3H, =C—OCH$_3$) 4.30 (S,2H, —CH$_2$—) 5.82 (S,1H, OH) 6.58–6.92 (m, 3H, =CH).

Ultimate analysis: C$_9$H$_{12}$O$_3$ Calculated value: C, 64.27%; H, 7.19%, Measured value: C, 64.30%; H, 7.25%.

EXAMPLES 2 to 15

Fifteen kinds of alkoxyphenols were prepared in the same manner as in Example 1 except that the compounds listed in Table 1 below under the reacting conditions specified therein are used.

TABLE 1

| Ex. | Starting material | Alkali metal hydroxide and dewatering agent | Alcohol | Temperature (°C.) | Time (hr) | Alkoxyphenol | Yield (%) |
|---|---|---|---|---|---|---|---|
| 2 | 2-chlorophenol | NaOH CaO | $CH_3OH$ | 110–115 | 5 | 2-methoxyphenol | 92 |
| 3 | 2-bromo-phenol | NaOH CaO | $CH_3OH$ | 110–120 | 6 | 2-methoxyphenol | 94.5 |
| 4 | 2,4,6-tribromo-phenol | NaOH CaO | $CH_3OH$ | 120–125 | 5 | 2,4,6-trimethoxy-phenol | 90.5 |
| 5 | 2-chloro-4-methylphenol | KoH CaO | $CH_3OH$ | 110–120 | 5 | 2-methoxy-4-methylphenol | 91.4 |
| 6 | 2-bromo-4-tert-butylphenol | NaOH CaO | $CH_3OH$ | 110–120 | 5 | 2-methoxy-4-tert-butylphenol | 89.7 |
| 7 | 2-bromo-4-tert-butylphenol | NaOH CaO | $C_2H_5OH$ | 100–110 | 6 | 2-ethoxy-4-tert-butylphenol | 75.6 |
| 8 | 2-bromo-4-tert-butylphenol | NaOH CaO | tert-$C_4H_9OH$ | 100–110 | 6 | 2-tert-butoxy-4-tert-butylphenol | 73.5 |
| 9 | 2-bromo-4-formylphenol | NaOH CaO | $CH_3OH$ | 110–120 | 3 | 2-methoxy-4-formylphenol | 94 |
| 10 | 2-chloro-4-hydroxymethyl-phenol | NaOH CaO | $CH_3OH$ | 110–120 | 4 | 2-methoxy-4-hydroxymethyl-phenol | 92 |
| 11 | 2-bromo-4-acetoxymethyl-phenol | NaOH CaO | $CH_3OH$ | 110–120 | 3 | 2-methoxy-4-acetoxymethyl-phenol | 91.5 |
| 12 | 2,6-dibromo-4-acetoxymethyl-phenol | NaOH CaO | $CH_3OH$ | 110–120 | 4 | 2,4-dimethoxy-4-acetoxymethyl-phenol | 89.5 |
| 13 | 2,6-dibromo-4-acetoxymethyl-phenol | NaOH CaO | $C_2H_5OH$ | 110–120 | 3 | 2,6-diethoxy-4-acetoxymethyl-phenol | 73.7 |
| 14 | 2,4,6-trichloro-3-hydroxymethyl-phenol | NaOH CaO | $CH_3OH$ | 120–125 | 4 | 2,4,6-trimethoxy-4-hydroxymethyl-phenol | 88.6 |
| 15 | 2,4,6-trichloro-phenol | KoH CaO | $CH_3OH$ | 110–120 | 6 | 2,4,6-trimethoxy-phenol | 89.7 |
| Comp. Ex. | 2-bromo-4-formyl-phenol | Na | $CH_3OH$ | 110–120 | 3 | 2-methoxy-4-formylphenol | 93.5 |

COMPARISON EXAMPLE 2

Preparation of 2-methoxy-4-methoxymethylphenol was conducted in a similar manner as in Example 1 except that calcined calcium oxide (dehydrating agent) was not used. Sodium hydroxide (3.16 g, 79.1 m mole) was dissolved in 60 ml of methanol and the solution was refluxed for 12 hours. To the 30 ml of the resulting solution, 931 mg (4.1 m mole) of 2-bromo-4-methoxymethylphenol, 15 ml of dimethylformamide and 240 mg of anhydrous cupric chloride were added. The mixture was stirred at 110° to 118° C. under the nitrogen stream for 4.5 hours while evaporating the solvent.

The remaining solvent was further distilled off from the reaction mixture thus obtained. Then 5 ml of 5% HCl solution was added to the residue and the mixture was extracted with ether. The extract was washed with saturated sodium chloride solution and dried on anhydrous sodium sulfate. The liquid was developed with a mixture of hexane-benzene-ethyl acetate (20:20:1) on a silica gel column to produce 38.5 mg of 2-methoxy-4-methoxymethylphenol. Yield: 5.6%.

COMPARISON EXAMPLE 3

Sodium hydroxide (3.16 g, 79.1 m mole) was dissolved in 60 ml of methanol and the solution was refluxed for 12 hours. To the solution were added 750 mg (4.1 m mole) of 2-bromophenol and 240 mg of anhydrous cuprous chloride. Then the reaction was carried out in the same manner as in Comparison Example 2 for 5 hours while evaporating methanol. After the reaction was completed, 43.7 mg of 2-methoxyphenol was obtained in the same manner as in Comparison Example 2. Yield: 8.6%.

COMPARISON EXAMPLE 4

Sodium hydroxide (3.16 g, 79.1 m mole) was dissolved in 60 ml of methanol and the resulting solution was refluxed for 12 hours. To the solution were added 980 mg (4.1 m mole) of 2-bromo-4-t-butylphenol, 240 mg of anhydrous cupric chloride and 15 ml of dimethylformamide. Subsequently the reaction was conducted in the same manner as in Comparison Example 2 for 4.5 hours while heating the mixture at 110° to 115° C. under stirring to evaporate the solvent.

After the reaction was completed, 100 mg of 2-methoxy-4-t-butylphenol was obtained in the same manner as in Comparison Example 2. Yield: 13.6%.

EXAMPLE 16

To 11.6 g of calcined calcium oxide were added 100 ml (3.12 mol) of dried methanol and 3.5 g (0.0875 mol) of sodium hydroxide and then the mixture was refluxed for 6 hours on an oil bath. The mixture was left to stand and 50 ml of the supernatant was taken off from the reflux. The supernatant thus withdrawn was added to 692 mg (4 m mol) of 2 bromophenol. To the resulting solution were added 15 ml of dried dimethylformamide and 240 mg of anhydrous cupric chloride and the resulting mixture was placed in an reactor. While the bottom part of the reactor was dipped in an oil bath, the mixture was stirred for 4 hours at 110°–118° C. to evaporate the solvent.

The remaining solvent was further distilled off from the reaction mixture thus obtained. Then 50 ml of 5%

HCl iced solution was added to the residue and the resulting mixture was extracted with 300 ml of ether. The extract was washed with saturated sodium chloride solution and dried with anhydrous sodium sulfate. After removing ether, the product was distilled under vacuum to produce 476 mg of 2-methoxyphenol (96.0% in yield), b.p. 53°–55° C./4 mmHg.

EXAMPLE 17

To 11.6 mg of calcined calcium oxide were added 30 ml (0.9375 mol) of dried methanol and 3.5 g (0.0875 mol) of sodium hydroxide and then the mixture was refluxed for 5 hours on an oil bath. The mixture was left to stand and 15 ml of the supernatant was taken off from the reflux. The supernatant thus withdrawn was added to 890 mg (4.1 m mol) of 2-bromo-4-methoxymethylphenol. To the reulting mixture were added 15 ml of dried dimethylformamide and 240 mg of anhydrous cupric chloride and the resulting mixture was placed in an reactor. The mixture was stirred at 110°–118° C. for 4 hours on an oil bath to evaporate the solvent.

The remaining solvent was further distilled off under vacuum from the reaction mixture. Then 50 ml of 5% HCl iced solution was added to the above product and the resulting mixture was extracted with 300 ml of ether. The extract was washed with saturated sodium chloride and dried with anhydrous sodium sulfate. After removing ether from the dried extract, the resulting liquid was developed on a silica gel column in the same manner as in Example 1 to produce 628 mg (91.1% in yield) of 2-methoxy-4-methoxymethylphenol.

We claim:

1. A process for preparing an alkoxyphenol represented by the formula:

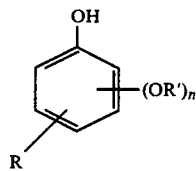

wherein R is hydrogen, alkyl having 1 to 4 carbon atoms, formyl, hydroxymethyl, alkoxymethyl, dialkoxymethyl, acetoxymethyl or diacetoxymethyl, R' is alkyl having 1 to 4 carbon atoms, and n is an integer of 1 to 5; characterized in that a phenol halide represented by the formula:

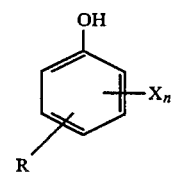

wherein R and n are as defined above, and X is chlorine or bromine is reacted, in the presence of a copper salt serving as a catalyst and a solvent, with a reaction product; wherein the reaction product is prepared by heating at reflux temperature of the solvent, in the presence of calcium oxide, 1 to 20 moles of an alkali metal hydroxide, per mole of the phenol halide, and 1 to 50 moles of a compound of the formula R'OH wherein R' is as defined above, per mole of the alkali metal hydroxide.

2. A process as defined in claim 1 wherein the calcium oxide is used in an amount of 0.5 to 50 times the weight of a phenol halide.

3. A process as defined in claim 1 wherein the product prepared by heating the alkali metal hydroxide and the alcohol in the presence of the dehydrating agent is separated from the calcium oxide after the heating and then reacted with the phenol halide.

4. A process as defined in claim 1 wherein the product prepared from the alkali metal hydroxide and the alcohol is used in an amount of about 1 to about 10 moles per mole of the phenol halide.

5. A process as defined in claim 1, wherein X is chlorine.

* * * * *